United States Patent
Singh et al.

(10) Patent No.: US 10,519,123 B2
(45) Date of Patent: Dec. 31, 2019

(54) PROCESS FOR PREPARATION OF AN AROMATIC N-GLYCIDYLAMINE

(71) Applicant: Grasim Industries Limited, Nagda (IN)

(72) Inventors: Ashok Kumar Singh, Taluka Panvel (IN); Prashant Samant, Taluka Panvel (IN); Alif Lalani, Taluka Panvel (IN); Mukesh Kathalewar, Taluka Panvel (IN); Vishnu More, Taluka Panvel (IN)

(73) Assignee: Grasim Industries Limited (IN)

( * ) Notice: Subject to any disclaimer, the term of this patent is extended or adjusted under 35 U.S.C. 154(b) by 0 days.

(21) Appl. No.: 16/074,931

(22) PCT Filed: Feb. 3, 2017

(86) PCT No.: PCT/IB2017/050584
§ 371 (c)(1),
(2) Date: Aug. 2, 2018

(87) PCT Pub. No.: WO2017/134609
PCT Pub. Date: Aug. 10, 2017

(65) Prior Publication Data
US 2019/0031632 A1    Jan. 31, 2019

(30) Foreign Application Priority Data

Feb. 4, 2016   (IN) .............................. 201621004041

(51) Int. Cl.
| | | |
|---|---|---|
| *C07D 301/27* | (2006.01) | |
| *C07D 301/32* | (2006.01) | |
| *C07D 303/36* | (2006.01) | |

(52) U.S. Cl.
CPC .......... *C07D 301/27* (2013.01); *C07D 301/32* (2013.01); *C07D 303/36* (2013.01)

(58) Field of Classification Search
CPC ... C07D 301/27; C07D 301/32; C07D 303/36
See application file for complete search history.

(56) References Cited

U.S. PATENT DOCUMENTS

| 4,540,769 A | 9/1985 | Dobinson et al. |
| 5,280,069 A | 1/1994 | Dobinson et al. |
| 5,362,849 A | 8/1994 | Dobinson et al. |

FOREIGN PATENT DOCUMENTS

| EP | 0 173 075 | * | 5/1985 |
| EP | 2143718 A1 | | 1/2010 |
| JP | S52214 A | | 1/1977 |
| JP | S62238278 A | | 10/1987 |
| WO | 2005/003109 | * | 1/2005 |
| WO | 2005003109 A2 | | 1/2005 |

OTHER PUBLICATIONS

European Patent Office, International Search Report and Written Opinion issued in corresponding PCT Application No. PCT/IB2017/050584, dated May 2, 2017 (11 pages).

* cited by examiner

*Primary Examiner* — D Margaret M Seaman
(74) *Attorney, Agent, or Firm* — Wood Herron & Evans LLP

(57) ABSTRACT

A process for preparing an aromatic N-glycidylamine comprising a step of heating a mixture of an amine having at least one aromatic aminohydrogen atom with at least 0.7 equivalent of epichlorohydrin per aminohydrogen equivalent of the amine in presence of a catalyst dissolved in an inert organic solvent, at a pressure in a range of 200 mbar to 600 mbar; and adding a base to the mixture at a pressure in a range of 200 mbar to 600 mbar to facilitate dehydrochlorination of product of the previous step to obtain the aromatic N-glycidylamine.

14 Claims, No Drawings

US 10,519,123 B2

PROCESS FOR PREPARATION OF AN AROMATIC N-GLYCIDYLAMINE

FIELD OF INVENTION

The present disclosure provides a process for preparation of N-glycidyl compounds. Particularly, the present disclosure provides a process for preparation of an aromatic N-glycidylamine.

BACKGROUND

Epoxy resins are suitable for a wide range of applications in industry as coatings, adhesives, encapsulants, moldings, laminates, castings, electrical insulation, weatherable coatings, sealants, impregnants, plasticizers, fibers, foams, and the like. Commonly used epoxy resin in such industries is diglycidyl ether of bisphenol. Epoxy resins having glycidyl groups linked to aromatic amino groups, for example, N,N,N',N'-Tetraglycidyl-4,4'-Diaminodiphenylmethane (TGDDM) are preferred in industries which require good performance at high temperatures such as aerospace industry. Such compounds are usually prepared by reacting an amine which contains at least one aromatic aminohydrogen atom with about 0.8 to 10 equivalents of epichlorohydrin per aminohydrogen atom, followed by conventional dehydrochlorination of the product so obtained using bases. The aromatic N-glycidylamine obtained from the process can be purified and cured by any known methods. The process can be carried out with or without a catalyst. For example, the process disclosed in the U.S. Pat. No. 4,540,769 involves use of an acidic catalyst. However, the disclosed process uses sodium flakes and is exothermic in nature and therefore not suitable for industrial production of the aromatic N-glycidylamine.

Further, the conventionally known processes for preparation of the aromatic N-glycidylamine either provide a highly viscous product or require long reaction time and/or high reaction temperature conditions and/or use solvents for the catalysts that require specific safety measures.

The highly viscous product is obtained due to secondary reactions taking place during the process. Examples of the secondary reactions include coupling reactions. To avoid drawbacks associated with the highly viscous product, inert or reactive diluents are used. However, the use of the inert or reactive diluents can adversely affect the properties of a cured resin. Further, if inert diluents are used then the same are required to be removed completely before curing due to their flammability or toxicity.

Therefore, there is a need of a process for preparation of the aromatic N-glycidylamine, which avoids the drawbacks associated with the conventional processes. Specifically, there is a need for a process that provides highly pure aromatic N-glycidylamine having lower viscosity. At the same time, it is desired that the process is rapid and has high yield. It is also desired that such process involves use of solvent(s) for the catalysts that do not require specific safety measures and produce fewer by-products such as oligomers.

SUMMARY OF INVENTION

The present disclosure relates to a process for preparing an aromatic N-glycidylamine. The process comprises a step of heating a mixture of an amine having at least one aromatic aminohydrogen atom with at least 0.7 equivalent of epichlorohydrin per aminohydrogen equivalent of the amine in presence of a catalyst dissolved in an inert organic solvent, at a pressure in a range of 200 to 600 mbar; and adding a base to the mixture at a pressure in a range of 200 to 600 mbar to facilitate dehydrochlorination of product of previous step to obtain the aromatic N-glycidylamine.

In accordance with an embodiment, the inert organic solvent is selected from a group consisting of methoxyethanol, 2-butoxyethanol, isodecanol, ethyleneglycol, diethyleneglycol, N-methylpyrrolidone, gamma butyrolactone, benzyl alcohol, dibutyl phthalate, butane-1,4-diol, ethyl methyl ketone, benzene, toluene and combination thereof.

DETAILED DESCRIPTION

For the purpose of promoting an understanding of the principles of the invention, reference will now be made to embodiments and specific language will be used to describe the same. It will nevertheless be understood that no limitation of the scope of the invention is thereby intended, such alterations and further modifications in the disclosed process and system, and such further applications of the principles of the invention therein being contemplated as would normally occur to one skilled in the art to which the invention relates.

It will be understood by those skilled in the art that the foregoing general description and the following detailed description are exemplary and explanatory of the invention and are not intended to be restrictive thereof.

Reference throughout this specification to "one embodiment" "an embodiment" or similar language means that a particular feature, structure, or characteristic described in connection with the embodiment is included in at least one embodiment of the present invention. Thus, appearances of the phrase "in one embodiment", "in an embodiment" and similar language throughout this specification may, but do not necessarily, all refer to the same embodiment.

The present disclosure relates to a process for preparation of N-glycidyl compounds. Particularly, the present disclosure provides a process for preparation of an aromatic N-glycidylamine. The process comprises heating a mixture of an amine having at least one aromatic aminohydrogen atom with at least 0.7 equivalent of epichlorohydrin per aminohydrogen equivalent of the amine in presence of a catalyst dissolved in an inert organic solvent, at a pressure in a range of 200 to 600 mbar; and adding a base to the mixture at a pressure in a range of 200 to 600 mbar to facilitate dehydrochlorination of product of previous step to obtain the aromatic N-glycidylamine.

In accordance with an embodiment, the amine is heated with at least 0.8 to 1.5 equivalent of the epichlorohydrin per aminohydrogen equivalent of the amine. In accordance with an embodiment, the amine is bis(4-aminophenyl) methane.

The epichlorohydrin and the catalyst can be added to the mixture all at once or in portions.

The heating of the mixture is performed at a temperature in a range of 50° C. to 100° C. In accordance with an embodiment, the heating is performed at a temperature in a range of 60 to 70° C. In accordance with an embodiment, at the time of the heating of the mixture, the pressure is maintained in a range of 200 to 400 mbar.

The heating of the mixture is carried out for 2 to 7 hours. In accordance with an embodiment, the heating of the mixture is carried out for 2 to 4 hours.

The inert organic solvent is selected from a group consisting of methoxyethanol, 2-butoxyethanol, isodecanol, ethyleneglycol, diethyleneglycol, N-methylpyrrolidone, gamma butyrolactone, benzyl alcohol, dibutyl phthalate, butane-1,4-diol, ethyl methyl ketone, benzene, toluene and a combination thereof. In accordance with a preferred embodiment, the inert organic solvent is 2-butoxyethanol.

The amount of catalyst used is in general 0.1 to 10 parts by weight per 100 parts by weight of the amine, in particular 0.4 to 2 parts by weight per 100 parts by weight of the amine. In a preferred embodiment, the catalyst is a divalent or a polyvalent metal salt of nitric acid. Examples of the catalyst include but are not limited to magnesium perchlorate, calcium perchlorate, zinc perchlorate, nickel perchlorate, magnesium nitrate, manganese nitrate, lanthanum nitrate, zinc nitrate, ytterbium nitrate, magnesium trifluoroacetate, manganese trifluoroacetate, nickel trifluoroacetate, vanadyl trifluoroacetate, magnesium trifluoromethanesulphonate, cobalt trifluoromethanesulphonate, lanthanum trifluoroacetate, lanthanum trifluoromethane sulphonate, magnesium trichloroacetate, magnesium-2,2-dichloropropionate and magnesium tribromoacetate. In an example, the catalyst is zinc nitrate. In another example, the catalyst is lanthanum nitrate.

In an embodiment, an inert aromatic organic solvent is added to the mixture prior to the heating. Examples of the inert aromatic organic solvent include but are not limited to toluene and xylene.

In some embodiments, the base is sodium hydroxide or potassium hydroxide. By way of an example, the base is 50% sodium hydroxide solution. In accordance with an embodiment, the base is mixed with a quaternary ammonium halide, which acts as a phase transfer catalyst. An example of the quaternary ammonium halide is benzyltrimethylammonium chloride.

In accordance with an embodiment, prior to adding the base, the mixture is maintained at a temperature in a range of 60 to 90° C. for a period of 3 to 7 hours, at a pressure in a range of 200 to 600 mbar.

After adding the base, the mixture is heated at a temperature in a range of 50° C. to 100° C. and at a pressure in a range of 200 to 600 mbar for 2 to 7 hours. Preferably, after adding the base, the mixture is heated at a temperature in a range of 50° C. to 80° C. and at a pressure in a range of 200 to 400 mbar for 3 to 6 hours.

In accordance with an embodiment the aromatic N-glycidylamine is N,N,N',N'-Tetraglycidyl-4,4'-Diaminodiphenylmethane (TGDDM).

After the dehydrochlorination, the mixture is washed with water to separate the mixture into an aqueous layer and an organic layer. The organic layer comprises the aromatic N-glycidylamine. The organic layer is separated to obtain the aromatic N-glycidylamine. Any conventional methods can be used to purify the aromatic N-glycidylamine Examples of such methods include washing with solvent/filtration and/or distillation. The aromatic N-glycidylamine can be cured by any conventional method.

The following Examples illustrate the disclosed process in detail.

EXAMPLES

Example 1

Bis(4-aminophenyl) methane, toluene and 50% lanthanum nitrate in 2-butoxyethanol are stirred and heated to 60 to 70° C. under a reduced pressure (200-400 mbar) followed by addition of epichlorohydrin over a period of 2 to 5 hours. After completion of epichlorohydrin addition, the mixture is maintained at 60 to 70° C. and then vacuum is released. A further portion of catalyst solution is added and the temperature is raised to 75 to 85° C. under reduced pressure. The mixture is then maintained under this condition for about 3 to 5 hours under constant stirring. The temperature is reduced to 60 to 70° C. and 50% aqueous benzyltrimethylammonium chloride is then added and the apparatus is set up for vacuum azeotrope. 50% aqueous sodium hydroxide is then added over a period of 1 to 3 hours, water being azeotroped out under vacuum (200-500 mbar). At the end of addition, azeotrope is continued for a further of 2 to 3 hours. Toluene and water are then added with stirring and aqueous and organic layer are separated by known method. The aqueous layer is discarded and organic layer is washed with 10% aqueous sodium dihydrogen phosphate. An organic mass so obtained is filtered through high flow. Toluene is evaporated under vacuum at reduced pressure. The aromatic N-glycidylamine has an epoxide content 8.82 g/eq (91% of theory) and viscosity of 4560 cPs.

Example 2

Bis (4-aminophenyl) methane, toluene and 50% lanthanum nitrate in 2-butoxyethanol are stirred and heated to 60 to 70° C. under a reduced pressure of 200 to 400 mbar followed by epichlorohydrin over a period of 2 to 4 hours at this reduced pressure. After completion of epichlorohydrin addition, the mixture is maintained at 60° C. at this reduced pressure and then vacuum is released. A further portion of catalyst solution is added and the temperature is raised to 75-85° C. at reduced pressure. The mixture is maintained under this condition for 3 to 5 hours under constant stirring. The temperature is reduced to 60 to 70° C. and 50% aqueous benzyltrimethylammonium chloride is then added and the apparatus is set up for vacuum azeotrope. 50% aqueous sodium is then added over a period of 1 to 3 hours, water being azeotroped out under vacuum (200-400 m bar, preferably 300-350 mbar). At the end of addition, azeotrope is continued for a further of 2-3 hours. Toluene and water are then added with vigorous stirring and the aqueous and organic layer are separated. The aqueous layer is discarded and organic layer is washed with 10% aqueous sodium dihydrogen phosphate. An organic mass so obtained is filtered through high flow. Toluene is evaporated down in vacuum at 110° C. at reduced pressure. The N-glycidylamine has an epoxide content 8.82 g/eq (91% of theory) and viscosity of 4662 cPs.

Example 3

Bis (4-aminophenyl) methane, toluene and 50% zinc nitrate in 2-butoxyethanol are stirred and heated to 60 to 70° C. under a reduced pressure of 200 to 400 mbar followed by epichlorohydrin over a period of 2 to 4 hours at this reduced pressure. After completion of epichlorohydrin addition, the mixture is maintained at 60 to 70° C. at this reduced pressure and then vacuum is released. A further portion of catalyst solution is added and the temperature is raised to 75 to 85° C. at reduced pressure. The mixture is maintained under this condition for 3 to 5 hours under constant stirring. The temperature is reduced to 60 to 70° C. and 50% aqueous benzyltrimethylammonium chloride is then added and the apparatus is set up for vacuum azeotrope. 50% aqueous sodium hydroxide is then added over a period of 1 to 3 hours, water being azeotroped out under vacuum (200 to 400 m bar, preferably 300 to 350 mbar). At the end of addition, azeotrope is continued for a further of 2 to 3 hours. Toluene and water are then added with vigorous stirring and the aqueous and organic layer are separated. The aqueous layer is discarded and organic layer is washed with 10% aqueous sodium dihydrogen phosphate. An organic mass is filtered through high flow. Toluene is evaporated down in vacuum at 110° C. at reduced pressure. The N-glycidylamine has an epoxide content 8.77 g/eq (91% of theory) and viscosity of 4302 cPs.

INDUSTRIAL APPLICABILITY

The disclosed process enables preparation of high quality aromatic N-glycidylamine compounds in a simple, rapid and economical manner. The process is of shorter duration compared to the conventional processes. The reaction of the amine with the epichlorohydrin requires 2 to 7 hours to complete. In some embodiment, the reaction is completed in 2 to 4 hours only. Further, the disclosed process as whole requires just 7 to 10 hours to complete. The disclosed process provides more than 90% yield of aromatic N-glycidylamine and fewer by-products such as oligomers. The aromatic N-glycidylamine obtained by said process is yellowish in colour and is in highly pure form with viscosity in a range of 3000 to 6000 cPs. In accordance with an embodiment, the aromatic N-glycidylamine obtained from the disclosed process is almost 98% pure.

We claim:

1. A process for preparing an aromatic N-glycidylamine comprising:
   a) heating a mixture of an amine having at least one aromatic aminohydrogen atom with at least 0.7 equivalent of epichlorohydrin per aminohydrogen equivalent of the amine in presence of a catalyst dissolved in an inert organic solvent, at a pressure in a range of 200 mbar to 600 mbar; and
   b) adding a base to the mixture at a pressure in a range of 200 mbar to 600 mbar to facilitate dehydrochlorination of product of step (a) to obtain the aromatic N-glycidylamine,
   wherein the heating of the mixture is carried out for 2 hours to 4 hours,
   wherein prior to adding the base, the mixture is maintained at a temperature in a range of 60° C. to 90° C. for a period of 3 hours to 7 hours, at pressure in a range of 200 mbar to 600 mbar, and
   wherein after adding the base, the mixture is heated at a temperature in a range of 50° C. to 100° C. and at the pressure in a range of 200 mbar to 600 mbar for 2 hours to 7 hours.

2. The process as claimed in claim 1, wherein the amine is heated with at least 0.8 to 1.5 equivalent of the epichlorohydrin per aminohydrogen equivalent of the amine.

3. The process as claimed in claim 1, wherein the heating of the mixture is performed at a temperature in a range of 50° C. to 100° C.

4. The process as claimed in claim 1, wherein the inert organic solvent is selected from a group consisting of methoxyethanol, 2-butoxyethanol, isodecanol, ethyleneglycol, diethyleneglycol, N-methylpyrrolidone, gamma butyrolactone, benzyl alcohol, dibutyl phthalate, butane-1,4-diol, ethyl methyl ketone, benzene, toluene and combinations thereof.

5. The process as claimed in claim 4, wherein the inert organic solvent is 2-butoxyethanol.

6. The process as claimed in claim 1, wherein the catalyst is a divalent or a polyvalent metal salt of nitric acid.

7. The process as claimed in claim 6, wherein the catalyst is selected from a group consisting of magnesium perchlorate, calcium perchlorate, zinc perchlorate, nickel perchlorate, magnesium nitrate, manganese nitrate, lanthanum nitrate, zinc nitrate, ytterbium nitrate, magnesium trifluoroacetate, manganese trifluoroacetate, nickel trifluoroacetate, vanadyl trifluoroacetate, magnesium trifluoromethanesulphonate, cobalt trifluoromethanesulphonate, lanthanum trifluoroacetate, lanthanum trifluoromethane sulphonate, magnesium trichloroacetate, magnesium-2,2-dichloropropionate and magnesium tribromoacetate.

8. The process as claimed in claim 1, wherein an inert aromatic organic solvent is added to the mixture prior to the heating.

9. The process as claimed in claim 8, wherein the inert aromatic organic solvent is selected from a group consisting of toluene and xylene.

10. The process as claimed in claim 1, wherein the base is selected from a group consisting of sodium hydroxide and potassium hydroxide.

11. The process as claimed in claim 1, wherein the base is mixed with a quaternary ammonium halide.

12. The process as claimed in claim 11, wherein the quaternary ammonium halide is benzyltrimethylammonium chloride.

13. The process as claimed in claim 1, wherein the amine is bis(4-aminophenyl) methane.

14. The process as claimed in claim 1 further comprising:
   a) washing the mixture after the dehydrochlorination with water to separate the mixture into an aqueous layer and an organic layer comprising the aromatic N-glycidylamine; and
   b) separating the organic layer comprising the aromatic N-glycidylamine; and
   c) purifying the aromatic N-glycidylamine.

* * * * *